United States Patent [19]

Price et al.

[11] 3,956,477

[45] May 11, 1976

[54] METHOD AND ERYTHROCYTE PREPARATION FOR REVERSE BLOOD GROUPING

[75] Inventors: Richard T. Price, Verona; Rita C. Prodell, West Orange; Stephen B. Friedman, Stanhope, all of N.J.

[73] Assignee: Akzona Incorporated, Asheville, N.C.

[22] Filed: June 8, 1973

[21] Appl. No.: 368,158

[52] U.S. Cl. ................................ 424/8; 23/253 TP; 424/3; 424/11; 424/12; 424/13
[51] Int. Cl.$^2$ .................. G01N 31/00; G01N 33/16
[58] Field of Search ................ 424/3, 8, 11, 12, 13; 23/253 TP

[56]  References Cited
UNITED STATES PATENTS

| | | | |
|---|---|---|---|
| 2,770,572 | 11/1956 | Eldon | 424/11 |
| 3,666,421 | 5/1972 | Price | 424/12 X |
| 3,714,345 | 1/1973 | Hirata | 424/3 |

FOREIGN PATENTS OR APPLICATIONS

| | | | |
|---|---|---|---|
| 159,400 | 6/1972 | Hungary | 424/11 |

OTHER PUBLICATIONS

Williams, et al., Methods in Immuno. & Immunochem., Acd. Press N.Y., Vol. I 1967, pp. 339–346.
Dodge, Arch. of Biochem. & Biophy. Vol. 100, 1963 p. 119.
Tullis, Blood Cells & Plasma Proteins, Acdemic Press, N.Y., 1953 pp. 52–53.
Benyo, Chem. Abs., Vol. 75, Aug. 30, 1971 p. 264 Ab. No. 61480b.
Benyo, Hungary, Abstract No. T/1731, Mar. 1971 1 p.
Poulik, Nature, Vol. 208, Nov. 27, 1965 p. 874.
Dodge, Arch. Biochem. & Biophys. Vol. 100, 1963 pp. 119–130.

*Primary Examiner*—V. D. Turner
*Assistant Examiner*—A. P. Fagelson
*Attorney, Agent, or Firm*—Francis W. Young; Philip M. Pippenger

[57]  ABSTRACT

Disclosed herein is a stable preparation of human erythrocytes for use in reverse blood typing comprising erythrocytes hemolyzed by gradual hypotonic hemolysis using a sequence of aqueous hypotonic buffers to form stroma wherein the stroma cells are in the form of discoid bodies having the reticular membrane of the cell substantially intact. The stroma reagent has been found to be highly stable and antigenic in the sense that it contains blood group antigens (carried on the stroma cells), and can be admixed with human blood serum or plasma to determine the presence of hemologous blood group antibodies.

11 Claims, No Drawings

METHOD AND ERYTHROCYTE PREPARATION FOR REVERSE BLOOD GROUPING

BACKGROUND OF THE INVENTION

Native erythrocytes and those treated by many prior art procedures useful for indirect hemagglutination testing such as blood typing suffer from the disadvantage that they deteriorate rapidly on storage so that for typing purposes they are considered useless after about 21 days and are required to be replaced. Examples of methods directed at stabilization of red blood cells include U.S. Pat. No. 3,714,345, to Hirata which describes an erythrocyte preparation wherein stabilization is accomplished by sequential exposure of the blood cells to dilute solutions of pyruvic aldehyde and formaldehyde. See also U.S. Pat. No. 3,715,427, also to Hirata. Literature of interest includes the following references: Ling, Brit. J. Haemat., Vol. 7, 1961 (pp. 229 – 302); Kabat, Exptl. Immunochem. CC Thomas, Springfield, Ill., 2nd Ed., 1961 (pp. 542 – 550); Chem. Abs., Vol. 55 (1961) pp. 27495; Vol. 65 (1966) pp. 20497, 20672; and, Ingraham, PSEBM Vol. 99, Nov., 1958 (pp. 452 – 456).

DESCRIPTION OF THE INVENTION

The invention is a stable preparation of human erythrocytes for use in reverse blood typing by immunochemical agglutination reaction between blood group antigens carried on the erythrocytes and homologous antibodies present in the blood plasma or serum to be tested. The erythrocytes are prepared by a process of gradual hypotonic hemolysis using a sequence of aqueous hypotonic buffers, i.e., the blood cells are washed in a first aqueous buffer and allowed to remain in contact with the buffer until osmotic equilibrium is reached with the buffer. Thereafter, the process is repeated or a buffer which is more hypotonic is employed. The process is continued until essentially complete hemolysis is obtained. The resulting stroma (slightly pink to off white in color) is characterized in that the stroma cells are generally in form of discoid bodies (i.e., the stroma is homogeneous) of approximately the same size as the unhemolyzed erythrocytes. The reticular membrane of the cell is generally intact, although small rupture zones may be present where hemoglobin and other internal cell components exited from the cell during the process of hemolysis. As the reticulum is believed to carry the blood group antigens, it is important that this membrane survive hemolysis generally intact so that the resulting stroma is sufficiently antigenic to agglutinate homologous antibodies contained in blood serum or plasma.

To aid in visualization of the agglutination test reaction, the hemolyzed erythrocytes are stained (e.g., red or blue) to contrast in color with the blood fluids to be tested. The preparation also contains, as an important component, an aqueous buffer solution which is generally isotonic to the stromatol erythrocytes, i.e., the buffer is matched generally with the fluids used to hemolyze the cell and thereby serves to minimize further leaching out, osmosis or removal of components of the cell. The degree of matching is not, however, as important as the fact that a buffer of some strength be employed. The buffer also functions to maintain the dispersibility of the stroma cells which aids in the avidity and sensitivity of the agglutination reaction. It is known, for example, that if distilled water is used instead of an aqueous buffer, the stroma cells exhibit some tendency to pack tightly together during processing and the preparation often fails to exhibit a consistent sensitivity. The buffer also serves as a carrier liquid for the stroma cells during storage and prior to use.

A further component of the preparation is an antibacterial agent (i.e., bactericide) which is inert to and does not participate in the agglutination reaction. It has been found that at all stages of processing and in the finished preparation the stroma cells are easily attacked by bacteria and greatly benefit, in the final preparation, from the presence of bactericide.

The invention arises from a fortuitous combination of several factors. Red blood cells are notorious for their lack of stability and tendency to decompose. As stated above, red cells used in reverse blood typing in blood banks must be discarded and replaced after 3 weeks. Numerous attempts have been made to apply various types of surface coating or treatments to the cells to increase their stability. The present invention proceeds upon the belief that decomposition of the cells is due at least in part to the isotonic conditions which must be maintained in the suspension liquid to minimize hemolysis. This in turn precludes the use of effective preservatives. Hemolysis of the blood cells produces a cellular structure which does not require rigid isotonic conditions and which enables the stroma cells to be maintained for long periods by use of effective preservatives. However, the process of hemolysis disrupts the cell and may remove enough of the blood group antigens so that the sensitivity of the resulting stroma is not sufficient to provide a reliable reverse typing test. It has been discovered that this problem can be overcome by gradual hypotonic hemolysis as described above and exemplified in Example I. While a generally gradual type of hypotonic hemolysis has been known and practiced heretofore (see Dodge et al., Archives of Biochemistry and Biophysics, Vol. 100, p. 119, 1963), the effect of such hemolysis on the antigenicity level of the cells has not been realized or appreciated. Thus, stromatic human erythrocytes have been found to be both stable and antigenic and can be employed in reverse blood typing tests.

Selection of blood for stroma preparation is based primarily on three factors; antigenicity, fragility of the blood cells, and the presence or absence of various human pathogens. Antigenicity is determined by adjusting a 2 ml. sample of blood of known blood type to 5% cell concentration using 0.9% saline solution. The diluted sample is challenged against serial dilutions (i.e., 1:2, 1:4, 1:8, . . ., 1:512) commercial typing antisera containing the homologous antibody, for 120 seconds reaction time. After 120 seconds, the blood sample should exhibit at least a 1+ agglutination level at an antisera dilution of 1:64 as determined by Gradwohl's Clinical Laboratory Methods and Procedures, Vol. 2, p. 1485, 1970. This figure represents, however, a minimum level of acceptability. Preferably, the blood should exhibit a 1+ agglutination level at antisera dilutions of 1:128 or higher.

Fragility of the blood cells is determined by an osmotic fragility test performed essentially as described in Gradwohl's Clinical Laboratory Methods and Diagnosis, Vol. 1, pp. 572 – 574. Essentially, this test involves subjecting samples of blood to saline solutions of progressively increasing hypotonicity and noting the NaCl concentration at which hemolysis sets in and is completed. To be acceptable, blood should be completely hemolyzed at 0.35% NaCl. However, blood which is completely hemolyzed at 0.75% NaCl or at high concentrations is too fragile and is unsuitable. With regard to the preceding fragility requirements, very general correlation has been discovered with the age of the blood since collection. Generally, blood selected should be at least 7 days old and preferably expired blood is employed which is from about 21 to 42 days old and is therefore unsuitable for use in blood banks or for transfusion purposes. Blood selected should also be free of common pathogens such as those connected with diseases such as malaria, syphilis, and hepatitis.

| Composition | | Suitable hypotonic Concentrations* |
|---|---|---|
| Phosphate buffer | NaCl<br>$Na_2HPO_4.7H_2O$<br>$KH_2PO_4$ | 40 – 150 imOsm |
| Borate | NaCl<br>Boric Acid<br>NaOH | 40 – 150 imOsm |
| Citrate | Sodium Citrate<br>$(Na_3C_6H_5O_7.2H_2O)$<br>Citric Acid(HOC—<br>COOH) $(CH_2COOH)_2.H_2O$ | 40 – 150 imOsm |
| Acetate | Na Acetate Trihydrate<br>$CH_3COONa.3H_2O$<br>Glacial Acetic Acid<br>$CH_3COOH$ | 40 – 150 imOsm |

*The ideal milliosmolarity (imOsm) is calculated by totaling the concentrations of all ionizable species in solution, neglecting deviations from ideal behavior. The concentration of 310 imOsm is a close approximation to isotonicity for red blood cells.

Generally, the osmotic strength of the hypotonic buffer employed to hemolyze the cells should be from about 20 imOsm to about 150 imOsm, but other hypotonic washes from 1 to 300 imOsm can be used. Other factors to be observed in preparing stroma include the pH of the hypotonic buffer solutions which should be from about 7.0 to 7.5, and preferably is about 7.4. During processing, the temperature of the buffer and blood being processed should not exceed about 25° C. and is kept at 5° C. when possible to avoid or minimize the possibility of bacterial contamination. Suitable agents which can be employed include:
 Chloramphemicol
 Sodium Penicillin
 Neomyocin Sulfate
 Streptomyocin Sulfate
 Phenyl mercuric borate
 Sodium ethylmecurithiosalicylate
 Thimerosal
 Sodium Azide
Suitable dyes for staining the stroma include:
 Evans Blue (Direct Blue 53) — Biological stain Matheson, Coleman & Bell, Norwood, Ohio
 Bests Carmine Stain Compound, Paragon C. & C. Company, Inc., New York 58, New York
 Trypan Blue, Matheson, Coleman & Bell, Norwood, Ohio
 Biebrich Scarlet (water soluble), Allied Chemical Co., National Aniline Division, New York, New York
 Thiazine Red R — Harleco (Hartman - Lordon Company), Philadelphia, Pennsylvania
 Neutral Red (Tolylene Red) — Matheson, Coleman & Bell, Norwood, Ohio, E. Rutherford, New Jersey
 Azocarmine G — Biological stain, Hartman-Lordon Company, Philadelphia, Pennsylvania A preferred embodiment of the invention is the use of the stroma preparation described above in combination with polyvinylpyrrolidone (PVP). For example, the stroma preparation and PVP can be used to form separate components of a test kit for performing reverse blood typing tests. In another embodiment, the PVP can be deposited as a spot of dried reagent on a test card, reconstituted by addition of blood fluid to be tested, and mixed with the stroma reagent. It has been discovered that the use of PVP greatly increases the sensitivity of the stroma reagent. For example, the stroma reagent generally exhibits a 1+ agglutination level when matched against a 1:64 dilution of commercial typing serum. When employed in combination with PVP, an equivalent agglutination level is demonstrated at dilution levels of the typing serum of 1:256 frequently 1:512. Most significantly in actual reverse typing tests, the stroma reagent failed to correctly type between 4 and 6% of serum samples tested whereas when employed in combination with PVP, all samples were correctly typed. Thus, when employed in combination with PVP, the stroma reagent of the invention is equivalent in sensitivity to the unhemolyzed red blood cells presently employed in reverse typing tests, and is superior in the sense that the stroma cells exhibit much greater stability. Additionally, the stroma cells do not have to be stored at low temperatures (e.g., 2°– 8° C.) whereas low temperature storage is required for reagents containing unhemolyzed cells.

The most suitable form of PVP for use in the invention is PVP K-90, a product of the GAF Corporation. This material has a molecular weight of about 360,000 g./mole. Other suitable types include K-60 and K-30 with molecular weights of 160,000 and 40,000, respectively. Other types of PVP with molecular weights within the range of from about 40,000 to about 360,000 can also be employed, although these are not believed to be commercially available at present. Optimum results are obtained when the reaction volume (serum plus stroma reagent) is about 1% with respect to K-90. Suitable ranges on a % by volume basis are: for K-90, from approximately 0.25% to 2.5%; for K-60, from 1.0% to 6%; and for K-30, from about 4% to about 12%.

The general application of PVP materials to agglutination reactions, and particularly to increase the sensitivity thereof is discussed in McClorry, Canadian Journal of Medical Technology, Vol. 20, pages 50 – 56 (1960).

The preparation of the invention, regardless of whether it is employed with PVP, generally contains from about 0.10% to 2.0% by weight of stroma cells. Where PVP is employed, the test procedure involves admixing the plasma or serum to be tested with the PVP (either in liquid or dried form) and subsequently admixing the PVP-blood fluid mixture with the stroma reagent. The materials are allowed to react for 120 seconds and the presence or absence of agglutination is determined. Even a slight agglutination is interpreted as a positive test for the presence of the homologous antibody.

The following examples are presented to illustrate and further describe the invention.

EXAMPLE I

BLOOD SELECTION

About 450 ml. of human blood (type B, $Rh_o$ positive) was collected. The blood was approximately 10 days old and had been preserved in acid-citrate-dextrose. To ascertain suitability for use in stroma preparation according to the invention, the blood was tested for sensitivity to the pressure of "anti-B" antibodies by challenging against serial dilutions of commerical anti-B typing serum obtained from the Dade Company, a division of Hospital Supply Corporation. A 2 ml. sample of blood was taken and adjusted to 5% cell concentration with 0.9% saline solution. The cell concentration was determined using a thrombocytocrit which was spun at 1700 × G for 15 minutes in a centrifuge. Master doubling (serial) dilutions of the anti-B typing sera were prepared up to a dilution of 1:512. Testing was carried out on a card having a flat, white, plastic-coated test surface by admixing 0.03 ml. of the blood cell suspension with 0.05 ml. of diluted typing sera, spreading the mixture over an area roughly the size of a quarter, and gently rocking the card in a figure-eight pattern for 120 seconds. At the end of 120 seconds, the reaction mixture was read to ascertain the agglutination level as described in the article by Gradwohl, Clinical Laboratory Methods and Procedures, Vol. 2, p. 1485, 1970. The results were as follows:

| Antisera Dilution | 1:2 | 1:4 | 1:8 | 1:16 | 1:32 | 1:64 | 1:128 | 1:256 | 1:512 |
|---|---|---|---|---|---|---|---|---|---|
| Agglutination rating | 4+ | 4+ | 4+ | 3+ | 3+ | 2+ | 1+ | —+ | — |

To be acceptable for stroma production, the blood should exhibit at least 1+ agglutination level at a dilution of 1:64 by the end of the 120 second reaction period. Blood of a lesser sensitivity can be employed if desired; however, the stroma produced from this type of material will be less sensitive than if more antigenic whole blood cells were employed.

In addition to testing for sensitivity to commercial typing antisera, the blood was also known to be free of common pathogens such as those produced in malaria and syphilis, and had also been tested by counter immuno electrophoresis to detect hepatitis associated antigen.

An osmotic fragility test was also performed on the blood to determine the resistance of the red cells to hemolysis. The test procedure employed was essentially as described in Gradwohl, Clinical Laboratory Methods and Diagnosis, Vol. 1, pages 572–574, and, with slight modification was carried out as follows: a series of stock solutions of aqueous NaCl were prepared ranging in concentrations from 0.90% NaCl to 0.20% NaCl with intermediate concentrations at 0.85%, 0.80%, etc., at intervals of 0.05% NaCl. The saline solutions were placed in appropriately labeled test tubes. Four mls. of blood was adjusted to 40% cell concentration using a thrombocytocrit. This suspension was added in 0.2 ml. aliquots to each of the saline solutions, the tubes were inverted twice to suspend the cells, and were refrigerated for 12 hours at about 5° C. The results, read visually at the end of the storage period, showed some incidence of hemolysis at 0.65% NaCl (a yellow-orange coloration of the saline suspension) with hemolysis being complete at 0.50% NaCl, i.e., the supernatant was dark red and lower concentrations of NaCl did not produce supernatants which were more intense in color. Generally, blood which shows complete hemolysis by 0.75% NaCl or above is unsuitable in that the resulting stroma is insensitive to the corresponding antibody. Conversely, blood which does not show complete hemolysis by 0.35% NaCl is not generally employed in that processing to produce stroma may require a large number of washes with hypotonic buffer to produce stroma. To avoid damaging blood group antigens and decreasing sensitivity of the stroma, the number of washings to complete hemolysis should be kept at a minimum. Also, to facilitate processing where a number of different blood samples are to be hemolyzed to produce stroma, the fragility of the cells in bloods pooled is matched as closely as possible to eliminate extra washes needed to hemolyze samples of blood having cells which are less fragile.

PRODUCTION OF STROMA

Following testing, the blood sample was centrifuged at room temperature at about 1700 × G for 15 minutes to separate the red blood cells. The plasma and a white buffy material above the red cell pack were suctioned with a pasteur pipette attached to a suction flash and the red cell pack was washed by suspending in isotonic phosphate buffer of the following composition: 2.045 gm. NaCl, 4.76 gm. of $KH_2PO_4$, 9.38 gm. of $Na_2HPO_4.7H_2O$ in sufficient distilled water to provide a 1 liter solution which is adjusted to pH 7.4 with either NaOH or HCl. The suspension was agitated gently to achieve homogeniety and was spun down at 1700 × G for 15 minutes, and the supernatant was separated and discarded. The wash procedure was repeated until the supernatant contained no trace of red.

Following the last wash, the supernatant was suctioned off, and the red cells were hemolyzed by suspending in 0.01 M $PO_4$ buffer solution of the following composition: 0.5845 gm. NaCl, 1.3609 gm. $KH_2PO_4$, 2.6808 gm. $Na_2HPO_4.7H_2O$, in sufficient distilled water to provide 1 liter of buffer having an adjusted pH of 7.4. The red cell volume was approximately 310 ml. and the amount of hypotonic buffer used was about 3100 ml. The amount of buffer employed need not be exact and can be varied to fit the capacity of processing apparatus employed.

The hypotonic cell suspension was gently agitated at about 25° C. for about 1 hour and was stored overnight at 5° C. This procedure resulted in a gradual hemolysis in the sense that an osmotic equilibrium was believed to be established due to the extended contact time between the cells and the hypotonic buffer. This procedure is preferred, for example, over contacting the cells with a more hypotonic buffer (e.g., less than 0.01 molar $PO_4$) which would speedily hemolyze the cells, but which would also greatly disrupt the reticulum and perhaps even fragment the cells. Highly hypotonic buffers can be employed in the invention to complete the hemolysis where necessary, but these should be the last steps in a sequence following use of less hypotonic buffers. Optionally, if cells of relatively high fragility are employed, a different sequence of buffer concentrations may be required.

white background card and the extent of agglutination was read after 120 seconds. The results are set forth in the following table.

TABLE II

|  | 1:4 | 1:8 | 1:16 | 1:32 | 1:64 | 1:128 | 1:256 | 1:512 |
|---|---|---|---|---|---|---|---|---|
| Stroma without PVP | 4+ | 3+ | 2+ | 1+ | — | — | — | — |
| Stroma with PVP 1:1 | 4+ | 4+ | 3+ | 3+ | 2+ | 2+ | 1+ | 1+ |
| 1:1.5 | 4+ | 4+ | 3+ | 3+ | 2+ | 2+ | 1+ | 1+ |
| 1:2 | 4+ | 3+ | 3+ | 2+ | 2+ | 1+ | 1+ | 1+ |
| 1:2.5 | 4+ | 3+ | 3+ | 2+ | 1+ | 1+ | 1+ | ± |
| 1:3 | 4+ | 2+ | 2+ | 1+ | 1+ | 1+ | 1+ | ± |

Following storage, the cell suspension was spun down at 12,500 × G for 30 minutes at 10° C. It should be noted that in preparation of stroma, the exact processing temperatures employed are not critical, but temperatures in excess of about 25° C. encourage stroma decomposition and should be avoided. The supernatant (dark red color) was drawn off by Pasteur pipette connected to aspirator vacuum and the cell pack was resuspended in another 3000 ml. of 0.01 M $PO_4$ buffer, gently agitated for 1 hour, and was stored overnight at 5° C. Again, the developing stroma was separated by centrifugation at 12,500 × G for 30 minutes at 10° C. The supernatant was pink in color indicating that hemolysis was nearing completion. The stroma pack was resuspended in about 3000 ml. of a more hypotonic buffer (0.005 M $PO_4$) of the following composition: 0.2922 gm. NaCl, 0.6804 gm. $KH_2PO_4$, 1.3404 gm. $Na_2HPO_4.7H_2O$, in sufficient distilled water to yield 1 liter of buffer having an adjusted pH of 7.4. The suspension was stored overnight at 5° C. Following storage, the stroma was again spun down, separated and resuspended in hypotonic 0.005 M $PO_4$ buffer. The resulting clear supernatant was drawn off and the stroma was decanted into a vessel for dyeing and subsequent storage. Initial dyeing of the stroma is accomplished by adding 0.02 ml. of stock Evans Blue dye solution (0.5 g./50 ml. of 0.005 $MPO_4$ buffer) per milliliter of undiluted stroma. The stroma is then tested against serial dilutions of the appropriate antisera and examined for intensity of staining in the stroma agglutinates throughout the series of dilutions and for the presence of any excess dye in the reaction liquid. Increments of 0.005 ml. of stock dye solution per ml. of stroma are added if the stroma appears lightly dyed and no excess dye is noted in the reaction liquid. The dye employed was Evans Blue (Direct Blue 53), manufactured by Matheson, Coleman & Bell of Norwood, Ohio.

TESTING THE STROMA

Using the 0.005 molar $PO_4$ buffer described above, the dyed stroma was diluted: 1:1, 1:1.5, 1:2, 1:2.5, and 1:3. These dilutions were tested against serial dilutions of the commercial anti-B typing sera as described above. In carrying out these tests, PVP (polyvinylpyrrolidone) was employed as an additive in some of the tests to increase the sensitivity of the stroma. The PVP (molecular weight approximately 360,000) was employed in the form of a dried deposit (4.3% PVP in 0.005 molar $PO_4$ buffer) resulting from drying 0.03 ml. of the PVP solution on a white test card. The test was performed by reconstituting the PVP "dried-dot" with 0.10 mls. of diluted typing serum and reacting the resulting mixture with 0.03 mls. of diluted stroma suspension. The mixed reagents were rocked on the PVP By comparing the five dilutions of stroma, the best sensitivity was demonstrated at stroma dilutions of 1:1, 1:1.5, and 1:2. Sensitivity is the primary criteria in selecting the stroma. However, in view of the equivalent sensitivity in the above runs, the most economical use of stroma resulted from selecting a 1:2 stroma dilution. Therefore, sufficient 0.005 molar $PO_4$ buffer was added to the stroma batch to produce a 1:2 dilution. Sodium azide was added to a final concentration of 0.2% as a preservative.

EXAMPLE II

SERA* Testing With Liquid Stroma And Dried PVP

*either serum or plasma may be used.

Stroma reagents of blood types $A_1$ and B were prepared essentially as described in Example I. White background cards, each carrying a spot of dried PVP as described in Example I, were also employed. The blood group antibody contained in each of the serum samples was determined by testing each sample against Affirmagen Reagent Red Blood Cells, a product of Ortho Pharmaceutical Company. For both $A_1$ and B cells, the reactions were noted (positive or negative) and were also graded (1, 2, 3, 4).

Subsequently, each plasma sample was tested against the $A_1$ and B stroma of the invention. By the test procedure, 0.10 mls. of serum was used to reconstitute the dried PVP deposit on the white background card. Once reconstituted, 0.03 ml. of stroma was admixed thoroughly with the serum and PVP, the mixture was spread over a circular area having a diameter of approximately 3 cm., and was rocked gently. After 120 seconds, the agglutination reaction was read (positive or negative) and the level of reaction was also estimated (1, 2, 3, 4). The mass of the agglutination is generally less for the blood cells at a given reaction level than for the stroma. This is thought to result from the fact that the blood cell suspension is only 5% or so whereas the stroma suspension is more concentrated.

Comparison of test results showed correlation (positive or negative) of the stroma with the red cells in all 360 serum samples tested. If the grading of the reactions is compared, the red blood cells sometimes exhibited a stronger reaction with a particular sample than did the stroma cells, particularly where the reaction involved was strong. For example, several 4 plus agglutinations with red blood cells appeared to be 3 plus agglutinations with the stroma. However, in normal testing in blood banks or hospitals, only positive and negative characteristics of the reactions are generally considered.

In the preceding example, the PVP white background card was prepared by depositing 0.03 ml. per card of a 4.3% PVP solution in 0.005 molar PO₄ solution. This deposit was then air dried.

EXAMPLE III

Using type B Ortho Affirmagen Red Blood Cells, 154 sera were identified as containing antibody to B antigen. Employing liquid stroma prepared essentially as described in Example I, but without using PVP, 148 (96.2%) of the samples were identified as containing antibody to B antigen.

EXAMPLE IV

This example illustrates the use of the liquid stroma reagent of the invention with PVP also in liquid form rather than in the form of a dried deposit as in Example II. Using Ortho Affirmagen Red Blood Cells, 160 sera were reverse typed, 68 being type O, 62 being type B, 28 being type A, and 2 being type AB. The sera samples were tested against type $A_1$ and B stromas prepared essentially as in Example I by placing 0.03 ml. of 5.32% PVP solution on a white background card, admixing 0.10 ml. of serum, and adding 0.03 ml. of stroma. The reactions were read (positive or negative) after rocking the card gently for 120 seconds. Of the samples tested, 154 (96.3%) agreed with the test results using red blood cells. Four type O and 2 type B did not correspond with the results using red blood cells.

EXAMPLE V

Stability Of Stroma Reagent

Samples of stroma prepared essentially as in Example I were stored at four different temperatures and tested periodically to determine if any loss of sensitivity occurs during long term storage. The samples were stored at 2° – 8° C., 25° C., 37° C., and 45° C. The higher temperatures (37° C., 45° C.) were considered to represent conditions for accelerated aging and are higher than temperatures generally encountered in testing laboratories. Samples at each temperature were tested at intervals of 2 and 5 days, 1, 2, 3, 4, and 6 weeks, and again at 3 months. For some samples, storage time had not yet reached 3 months and therefore data was not available.

The samples were tested for sensitivity against serial dilutions of the appropriate type (anti-A or annti-B) of commercial typing sera. This procedure is described in Example I.

Using a type B stroma, and testing for sensitivity without the presence of PVP, the following results have been obtained after 3 months. It should be noted that a suitable stroma (sufficiently sensitive for use in hospitals, blood banks, etc.) must exhibit at least a 1+ reaction at antisera dilutions of 1:64.

a. At 2° – 8° C., sensitivity decreased from a grade 1+ reaction to a 1+ reaction at serial dilutions of antisera of 1:64.

b. At 25° C. and 37° C., sensitivity decreased from 1+ at a dilution of 1:64 to a 1+ level at antisera dilutions of 1:32. The initial drop from 1:64 to 1:32 was observed at the 5 day interval and sensitivity did not decrease significantly for the remainder of the storage period. The failure of this aged stroma to react at antisera dilutions of 1:64 indicates that the stroma by itself is not acceptable after about 5 days and should be used in conjunction with PVP or a similar reagent.

c. At 45° C., sensitivity decreased from 1+ at 1:64 to 1+ at 1:32 after 5 days and further decreased until after 3 months, the sensitivity was 1+ at antisera dilutions of 1:16. Sensitivity of this aged reagent would be unacceptable unless used in combination with PVP.

EXAMPLE VI

Stability Of Stroma With Polyvinylpyrrolidone

As in Example I, the stroma samples were aged at 4 different temperature levels (2° – 8° C., 25° C., 37° C., and 45° C.). Using PVP in the form of a dried deposit on a white background card, the stroma were tested as in Example II against serial dilutions of commercial typing serum. The initial reaction level (1+ at 1.256 antisera dilution) was found after 4 weeks to be unchanged at all 4 storage temperatures. Significantly, even accelerated aging at 45° C. had not decreased sensitivity. Data was not available for aged sensitivity at the 3 month level.

What is claimed is:

1. A stable preparation of human erthrocyte stroma for use in reverse blood typing comprising (a) the stroma of human erythrocytes prepared by hemolyzing a given quantity of erythrocytes by hypotonic hemolysis using a sequence of progressively less concentrated aqueous hypotonic buffers to form stroma wherein the stroma cells are generally in the form of discoid bodies having the reticular membrane of the cell substantially intact, said reticulum carrying an amount of blood group antigens which is sufficient to enter into agglutination reaction when contacted with human blood serum or plasma to be tested to indicate the presence therein of homologous blood group antibodies, the reticulum of said hemolyzed erythrocytes being stained to contrast in color with the blood fluids to be tested and thereby aid in visualization of the agglutination reaction; (b) an aqueous buffer solution which is approximately isotonic to the stromatal erythrocytes, maintains the dispersibility thereof, and serves as a carrier liquid for the stroma during storage and prior to use; and (c) an antibacterial agent which impedes bacterial attack upon the stroma and is inert to the agglutination reaction.

2. The preparation of claim 1 wherein the erythrocytes are from expired blood.

3. The preparation of claim 1 wherein the hypotonic buffer employed to hemolyze the erythrocytes has an osmotic strength of from about 20 to about 150 ideal milliosMoles.

4. The preparation of claim 1 in which the hypotonic buffer has a pH of about 7.4.

5. The preparation of claim 1 wherein the hypotonic buffer is a phosphate buffer.

6. A test method for reverse blood typing of human blood comprising admixing and reacting human serum or blood plasma from a blood sample to be tested with a preparation comprising (a) the stroma of human erythrocytes prepared by hemolyzing a given quantity of erythrocytes by hypotonic hemolysis using a sequence of progressively less concentrated aqueous hypotonic buffers to form stroma wherein the stroma cells are generally in the form of discoid bodies having the reticular membrane of the cell substantially intact, said reticulum carrying an amount of blood group antigens which is sufficient to enter into agglutination reaction when contacted with human blood serum or plasma to be tested to indicate the presence therein of homologous blood group antibodies, the reticulum of said hemolyzed erythrocytes being stained to contrast in color with the blood fluids to be tested and thereby aid in visualization of the agglutination reaction; (b) an aqueous buffer solution which is approximately isotonic to the stromatal erythrocytes, maintains the dispersibility thereof, and serves as a carrier liquid for the stroma during storage and prior to use; and (c) an antibacterial agent which impedes bacterial attack upon the stroma and is inert to the agglutination reaction.

7. The method of claim 6 wherein the blood fluid is admixed with a sufficient amount of polyvinylpyrrolidone having a molecular weight in the range of about 40,000 to about 360,000 prior to admixture with the stroma preparation to increase the sensitivity of the test preparation to approximately that of unhemolyzed red blood cells.

8. The method of claim 6 wherein the stroma cells are carried in a phosphate buffer.

9. The method of claim 6 wherein the hypotonic buffer has a pH of about 7.4.

10. The method of claim 6 wherein the stroma is derived from expired human blood.

11. The method of claim 6 wherein the hypotonic buffer employed to hemolyze the erythrocytes has an osmotic strength of from about 20 to about 150 ideal milliosMoles.

* * * * *